United States Patent
Kim et al.

(10) Patent No.: US 10,906,036 B2
(45) Date of Patent: Feb. 2, 2021

(54) IN-VITRO DIAGNOSTIC APPARATUS HAVING CARTRIDGE

(71) Applicant: BIOMEDUX CO., LTD, Suwon-si (KR)

(72) Inventors: Jongwon Kim, Seoul (KR); Jihyoung Lee, Seoul (KR); Sang-Yoon Kim, Chuncheon-si (KR); Ahreum Park, Seoul (KR); Sihn-Ae Lee, Seongnam-si (KR); Inyoung Kim, Pyeongtaek-si (KR); Doohee Jeong, Chuncheon-si (KR)

(73) Assignee: BIOMEDUX CO., LTD, Suwon-si (KR)

( * ) Notice: Subject to any disclaimer, the term of this patent is extended or adjusted under 35 U.S.C. 154(b) by 284 days.

(21) Appl. No.: 16/071,897

(22) PCT Filed: Aug. 16, 2016

(86) PCT No.: PCT/KR2016/008950
§ 371 (c)(1),
(2) Date: Jul. 20, 2018

(87) PCT Pub. No.: WO2017/126761
PCT Pub. Date: Jul. 27, 2017

(65) Prior Publication Data
US 2019/0022648 A1    Jan. 24, 2019

(30) Foreign Application Priority Data
Jan. 21, 2016 (KR) .................. 10-2016-0007533

(51) Int. Cl.
*B01L 3/00* (2006.01)
*G01N 35/10* (2006.01)
(Continued)

(52) U.S. Cl.
CPC ......... *B01L 3/502715* (2013.01); *B01L 3/502* (2013.01); *B01L 3/50273* (2013.01);
(Continued)

(58) Field of Classification Search
None
See application file for complete search history.

(56) References Cited

U.S. PATENT DOCUMENTS

| 4,826,660 | A  | 5/1989  | Smith et al. |
| 8,048,386 | B2 | 11/2011 | Dority et al. |

FOREIGN PATENT DOCUMENTS

| JP | 08010189 B2 | 1/1996 |
| JP | 05369043 B2 | 12/2013 |

(Continued)

*Primary Examiner* — Neil N Turk
(74) *Attorney, Agent, or Firm* — Kilpatrick Townsend & Stockton LLP (57) ABSTRACT

Provided is an in-vitro diagnostic apparatus having a cartridge. The cartridge includes a body to which a biochip is detachably coupled, and the body includes a plurality of sample accommodating chambers. The disc member includes a cylinder portion and a sample mixing chamber, wherein the cylinder portion has a hollow tube form and is coupled to the body, and the sample mixing chamber is disposed under the cylinder portion. A fluid input/output port is provided in a bottom portion of each of the sample accommodating chambers. The sample mixing chamber includes a fluid path and an injection path, the fluid path selectively connectable to the fluid input/output port, and the injection path connecting the sample mixing chambers with the biochip. A syringe piston is coupled to the cylinder portion and configured to slidably elevate along the cylinder portion.

5 Claims, 12 Drawing Sheets

(51) Int. Cl.
*G01N 35/02* (2006.01)
*C12Q 1/68* (2018.01)
*B01L 7/00* (2006.01)
*G01N 21/64* (2006.01)
*G01N 1/18* (2006.01)
G01N 1/28 (2006.01)
G01N 35/00 (2006.01)
G01N 35/04 (2006.01)

(52) U.S. Cl.
CPC ........... *B01L 3/502761* (2013.01); *B01L 7/00* (2013.01); *C12Q 1/68* (2013.01); *G01N 1/18* (2013.01); *G01N 21/64* (2013.01); *G01N 35/025* (2013.01); *G01N 35/10* (2013.01); *B01L 2200/10* (2013.01); *B01L 2300/0627* (2013.01); *B01L 2300/0803* (2013.01); *B01L 2300/0861* (2013.01); *B01L 2400/043* (2013.01); *B01L 2400/0421* (2013.01); *B01L 2400/0478* (2013.01); *B01L 2400/0487* (2013.01); *G01N 21/645* (2013.01); *G01N 2035/00158* (2013.01); *G01N 2035/00306* (2013.01); *G01N 2035/00326* (2013.01); *G01N 2035/00465* (2013.01); *G01N 2035/0484* (2013.01)

(56) References Cited

FOREIGN PATENT DOCUMENTS

| | | |
|---|---|---|
| KR | 10-0825087 B1 | 4/2008 |
| KR | 10-2012-0039345 A | 4/2012 |
| KR | 10-2013-0017718 A | 2/2013 |
| KR | 10-1239764 B1 | 3/2013 |

IN-VITRO DIAGNOSTIC APPARATUS HAVING CARTRIDGE

TECHNICAL FIELD

The present disclosure relates to a cartridge for extracting a biomaterial, which is the cartridge for use in an in-vitro diagnostic apparatus for diagnosing a biomaterial such as protein or DNA, and a diagnostic apparatus having the cartridge

BACKGROUND ART

In general, in order to diagnose the presence of a disease or gene abnormality in a human or an animal, a biomaterial such as DNA or protein is extracted and accommodated in a biochip formed of glass, silicon, metal, or plastic, and undergoes a gene amplification process. Then, the biochip is irradiated with light from a light source and the amount of light (fluorescence) generated from the biochip is analyzed for diagnosis.

Korean Patent No. 0825087 discloses an example of an apparatus employing the above-described method.

A biomaterial for use in a diagnostic apparatus is injected into a biochip and loaded in the diagnostic apparatus. As such, a device used to extract a specific biomaterial to be diagnosed from among biomaterials extracted from a living body and to inject the biomaterial into a biochip, is referred to as a cartridge.

According to the related art, extraction has not been performed as a cartridge is accommodated in a diagnostic apparatus. In general, there is a separate apparatus used to manufacture a biochip, and a biochip manufactured by the apparatus is input to a diagnostic apparatus manufactured for diagnosis and the diagnostic apparatus performs diagnosis only.

However, in the above method according to the related art, since the manufacture of a biochip and a diagnosis process of the biochip lack continuity, much time is spent for diagnosis. In other words, in an in-vitro diagnostic apparatus according to the related art, only a biochip prepared in advance is analyzed, and a biomaterial cannot be mixed in and input to a biochip. Accordingly, performing analysis may be inconvenient and take an unnecessarily large amount of time. Furthermore, since the manufacture and diagnosis of a biochip are performed by using separate equipment, the size of the equipment may increase and manufacturing costs may rise.

DETAILED DESCRIPTION OF THE INVENTIVE CONCEPT

Technical Problem

Provided is an in-vitro diagnostic apparatus having improved efficiency by providing a cartridge structure capable of easily manufacturing various biomaterial samples.

Technical Solution

According to an aspect of the present disclosure, an in-vitro diagnostic apparatus includes a cartridge including a body and a disc member, wherein a biochip is detachably coupled to the body, the body includes a plurality of sample accommodating chambers including a sectioned space for accommodating a plurality of fluids in a distributed manner, and the disc member is rotatably coupled to the body, wherein the disc member includes a cylinder portion and a sample mixing chamber, wherein the cylinder portion has a hollow tube form, is coupled to the body, and vertically penetrates through a center portion of the body, and the sample mixing chamber is located under the cylinder portion, wherein a fluid input/output port is provided in a bottom portion of each of the plurality of sample accommodating chambers, wherein the sample mixing chamber includes a fluid path and an injection path, the fluid path selectively connectable to the fluid input/output port, and the injection path connecting the sample mixing chamber with the biochip to allow a biomaterial prepared in the sample mixing chamber to be injected into the biochip, wherein a syringe piston is coupled to the cylinder portion and is configured to slidably elevate along an inner circumferential surface of the cylinder portion, wherein the disc member is rotatable by a disc rotating motor with respect to the body, wherein the disc member is rotatable by being caught by a rotation member, wherein the rotation member includes a protruding step, and a clutch groove portion is provided on a lower surface of the disc member, the clutch groove portion being caught by the protruding step; a case; a light source portion provided inside the case and generating visible light; a lens portion focusing light emitted from the light source portion and reflected by the biochip; an optical filter portion allowing only light of a specific wavelength band among light focused by the lens portion to pass therethrough; a photodiode sensor configured to detect light that passed through the optical filter portion; a disc rotating motor configured to rotate the disc member with respect to the body; and an elevation motor configured to elevate the syringe piston, wherein the optical filter portion is rotatable by a filter rotating motor that is fixed to the case, wherein the light source portion includes a plurality of light-emitting diodes arranged spaced apart from each other in a circular form, the plurality of light-emitting diodes being arranged such that light emitted from the plurality of light-emitting diodes converges to a single focal point.

Advantageous Effects of the Inventive Concept

Since the cartridge for an in-vitro diagnostic apparatus according to the present disclosure includes a body having a sample accommodating chamber sectioned into a plurality of spaces and a disc member rotatably coupled to the body and configured to selectively transfer a fluid including a biomaterial between the sample accommodating chamber and the sample mixing chamber by using a syringe, the biomaterial prepared in the sample mixing chamber may be directly injected into a biochip, and thus it is not necessary to prepare a separate biochip, and a continuous process of preparation of a biochip for diagnosis may be possible within a single diagnostic apparatus.

In the in-vitro diagnostic apparatus according to an embodiment of the present disclosure, since an electromagnet is applied to a magnetic system that magnetically interacts with a bead for accurate extraction of a biomaterial to be used for diagnosis, a magnetic force may be generated only when necessary, thereby improving accuracy of extraction of a biological sample.

Furthermore, in the in-vitro diagnostic apparatus according to an embodiment of the present disclosure, even when the type of a biomaterial to be diagnosed is changed, an optical filter that transmits a wavelength of light generated from the biomaterial may be rapidly and easily replaced by a rotatable optical filter portion.

BEST MODE

Embodiments of the present disclosure will now be described more fully with reference to the accompanying drawings.

Figure 1:
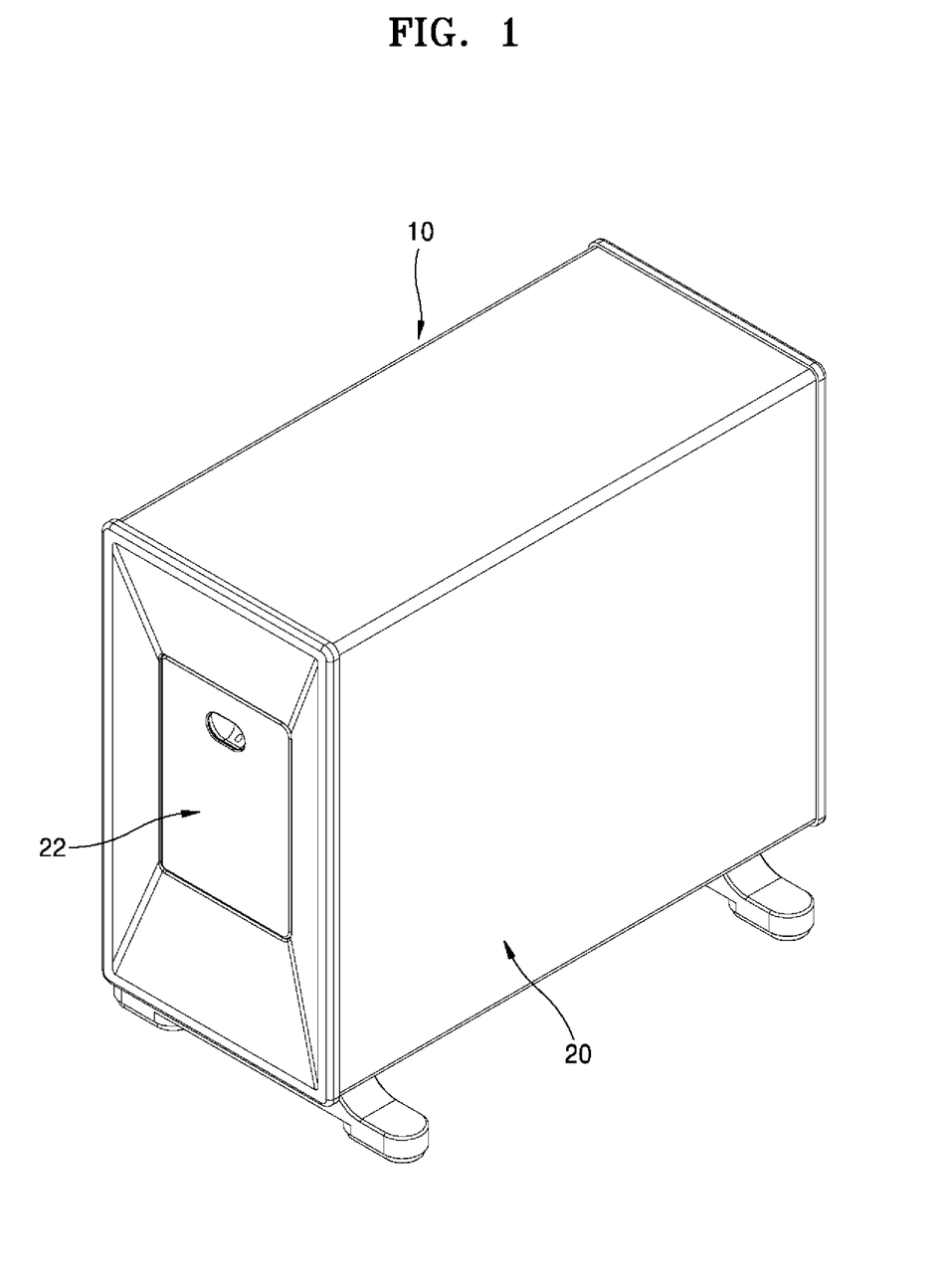
FIG. 1 illustrates an exterior of an in-vitro diagnostic apparatus according to an embodiment of the present disclosure.
Figure 2:
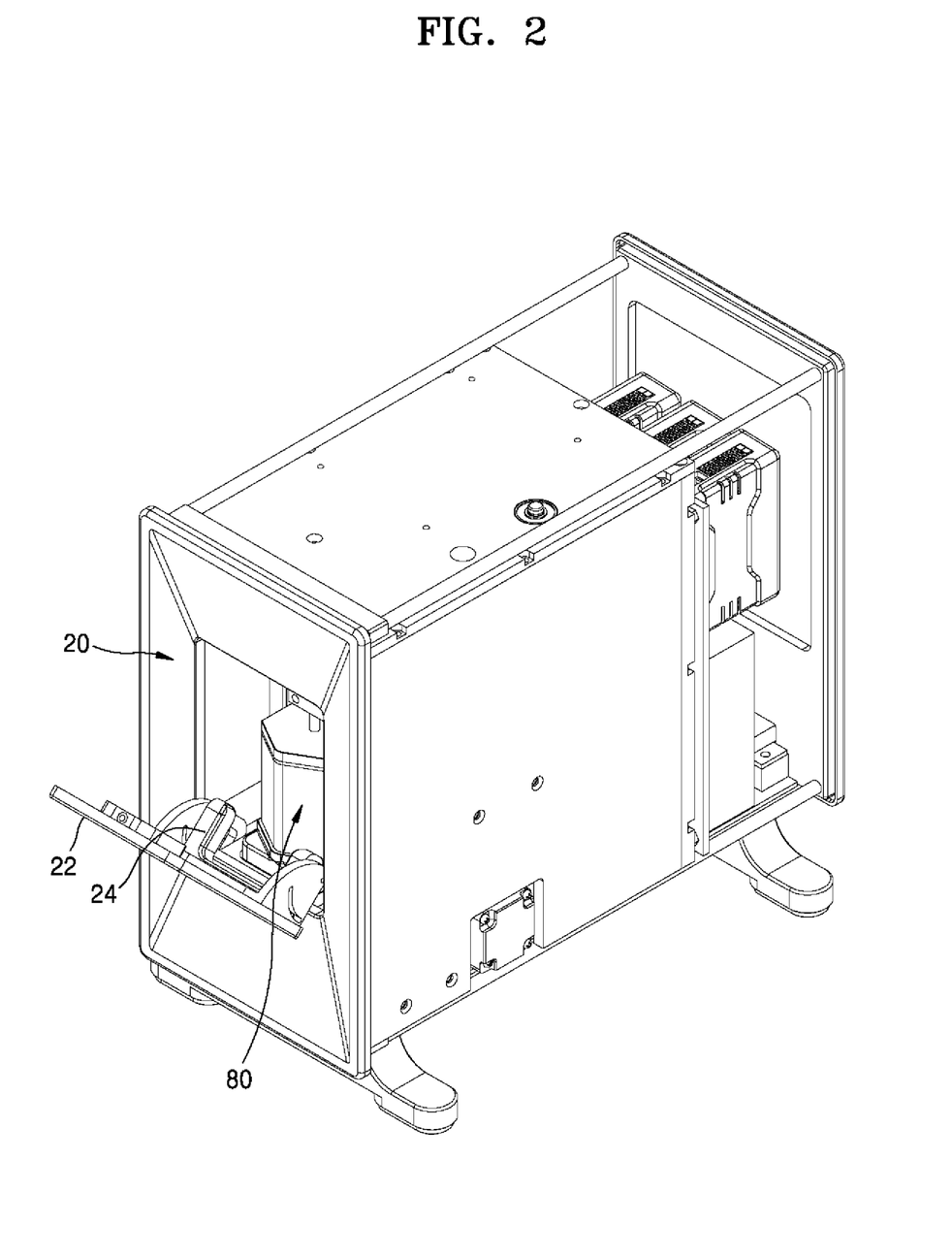
FIG. 2 illustrates a state in which a swing door of the diagnostic apparatus of FIG. 1 is opened.
Figure 3:
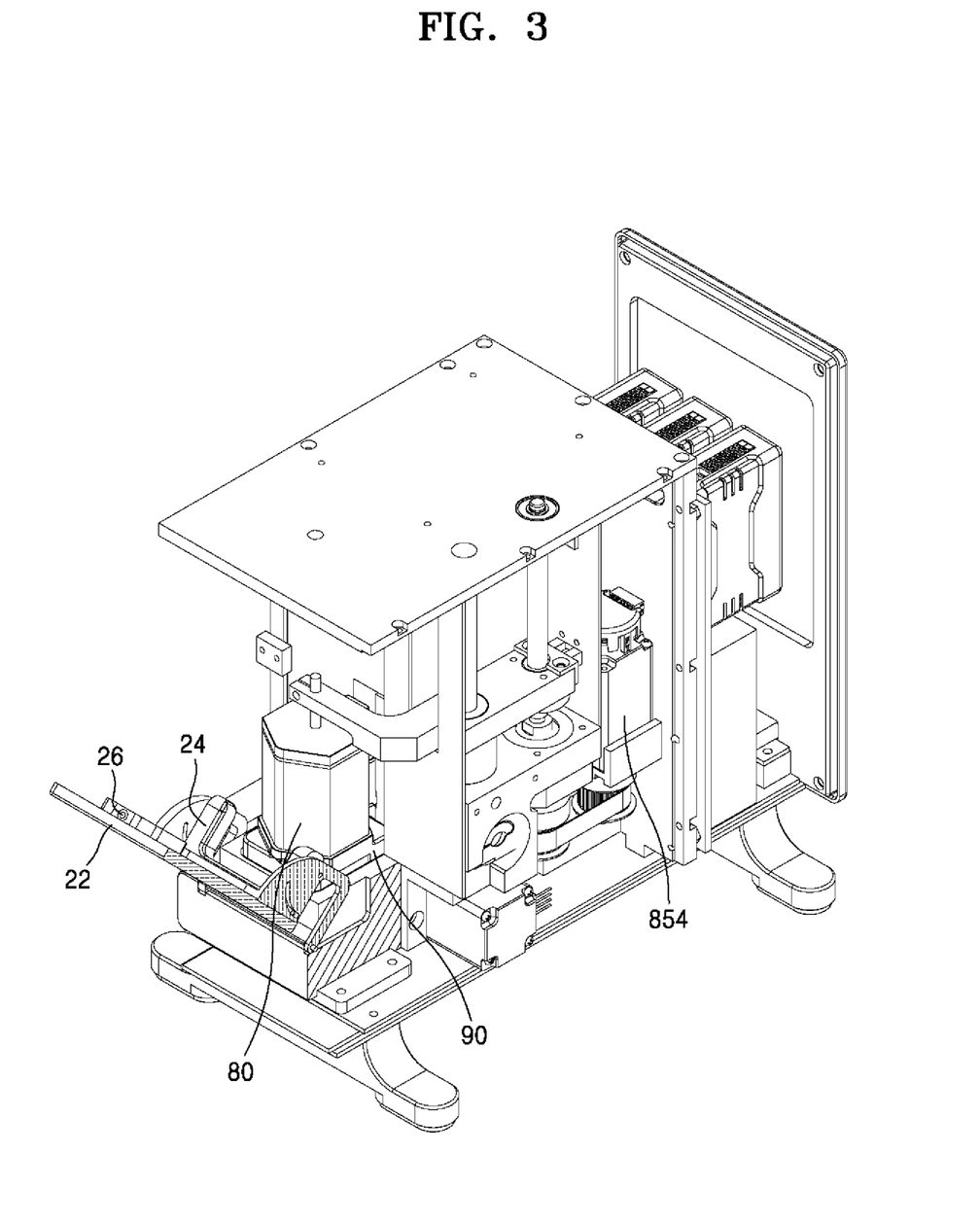
FIG. 3 illustrates an inner structure of the diagnostic apparatus of FIG. 1.
Figure 4:
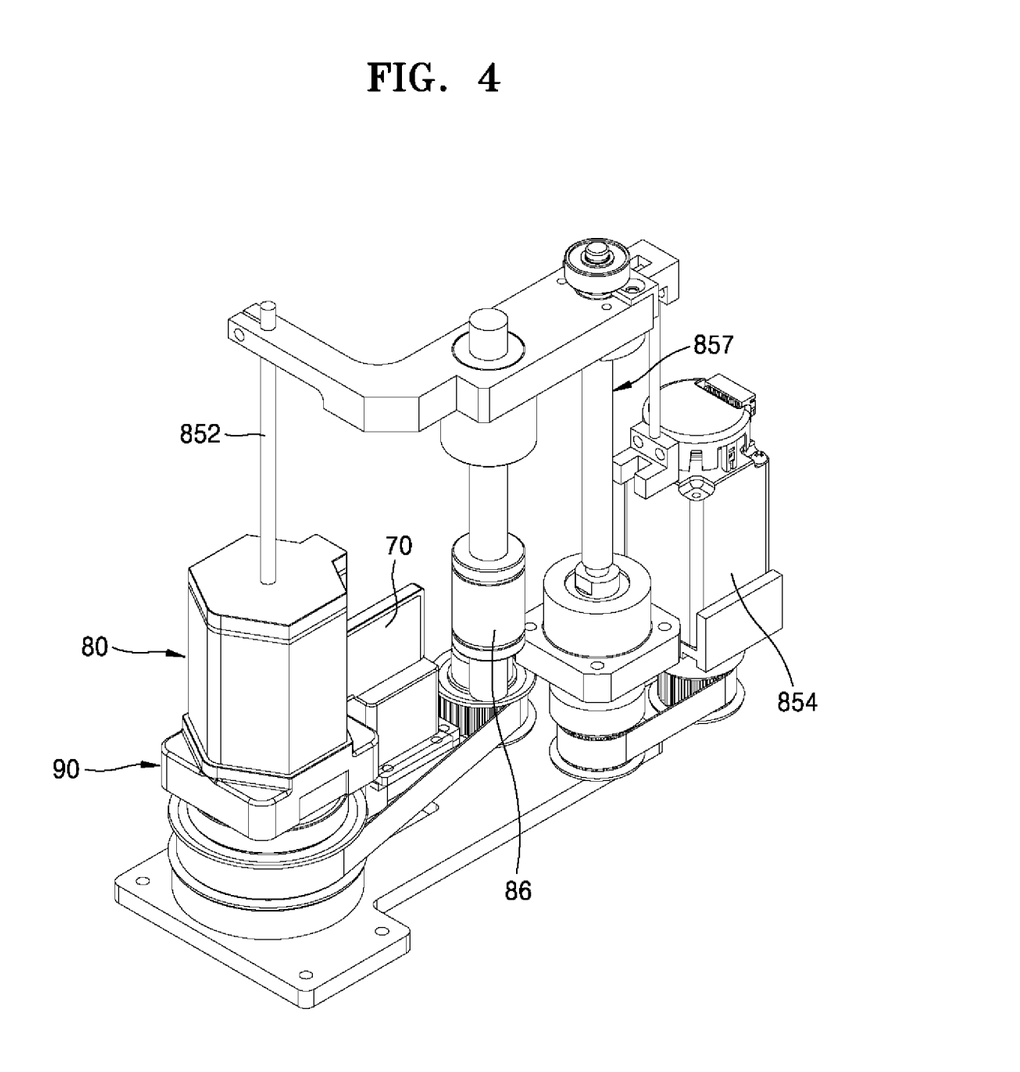
FIG. 4 illustrates a rotating and elevating structure of a cartridge in the diagnostic apparatus of FIG. 1.
Figure 5:
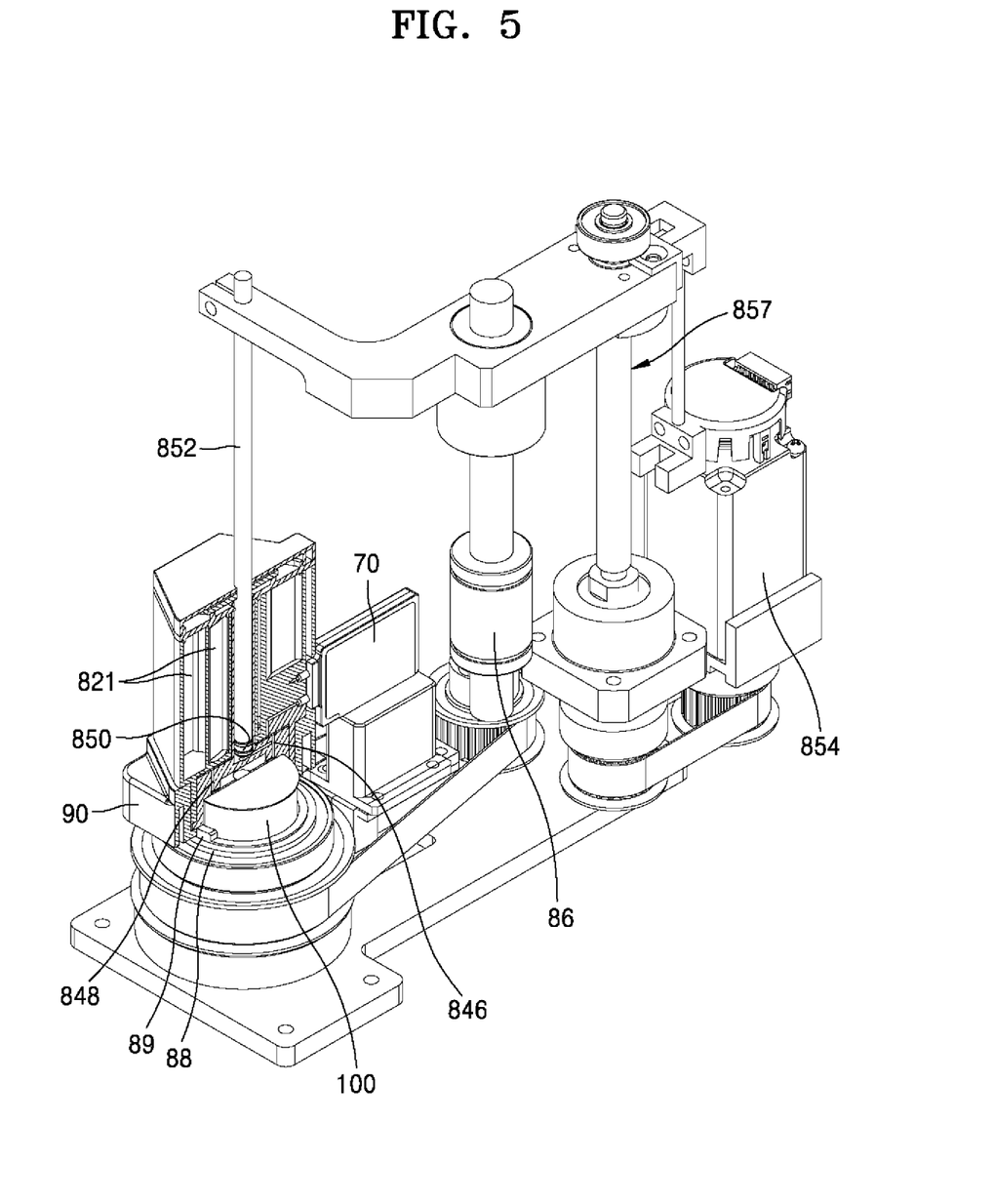
FIG. 5 is a partially cut-away view illustrating an inner structure of the rotating and elevating structure of the cartridge of FIG. 4.
Figure 6:
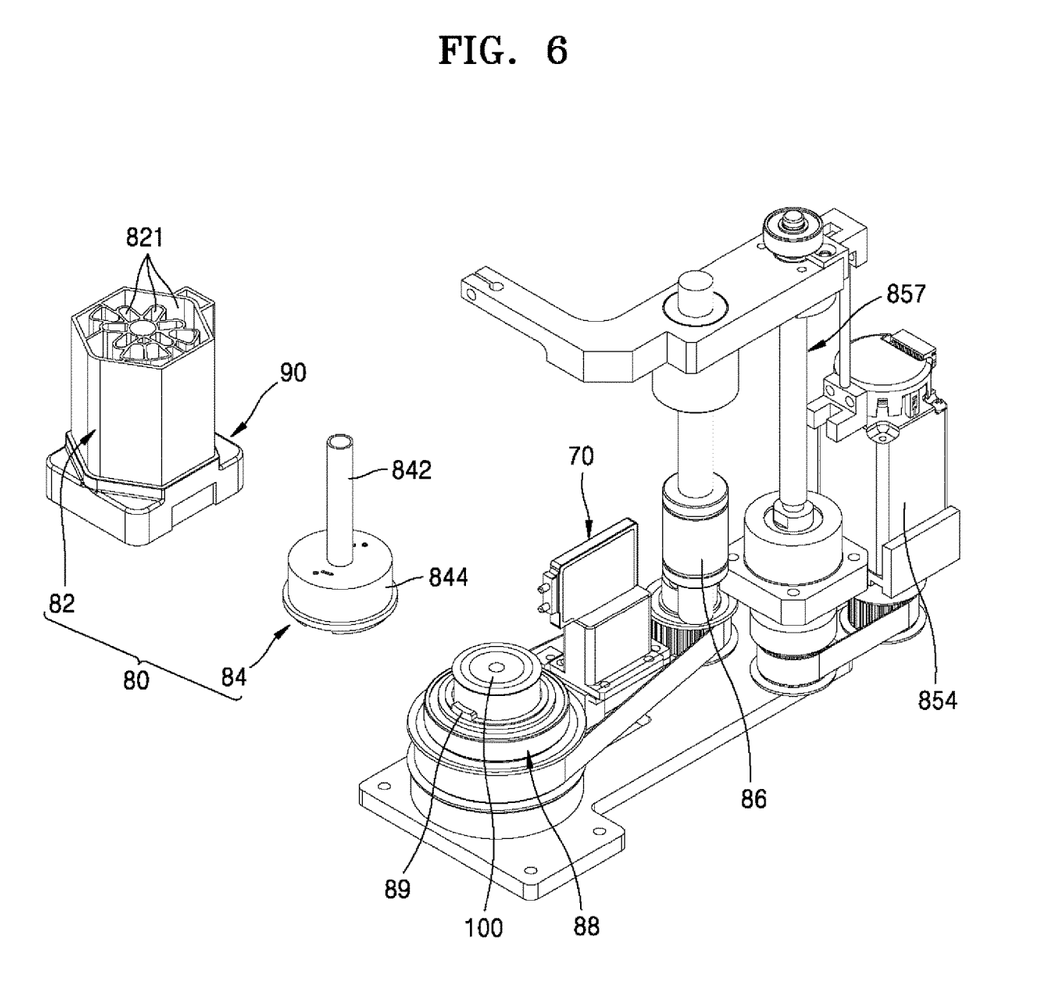
FIG. 6 is an exploded perspective view of constituent elements of the cartridge according to the present disclosure.
Figure 7:
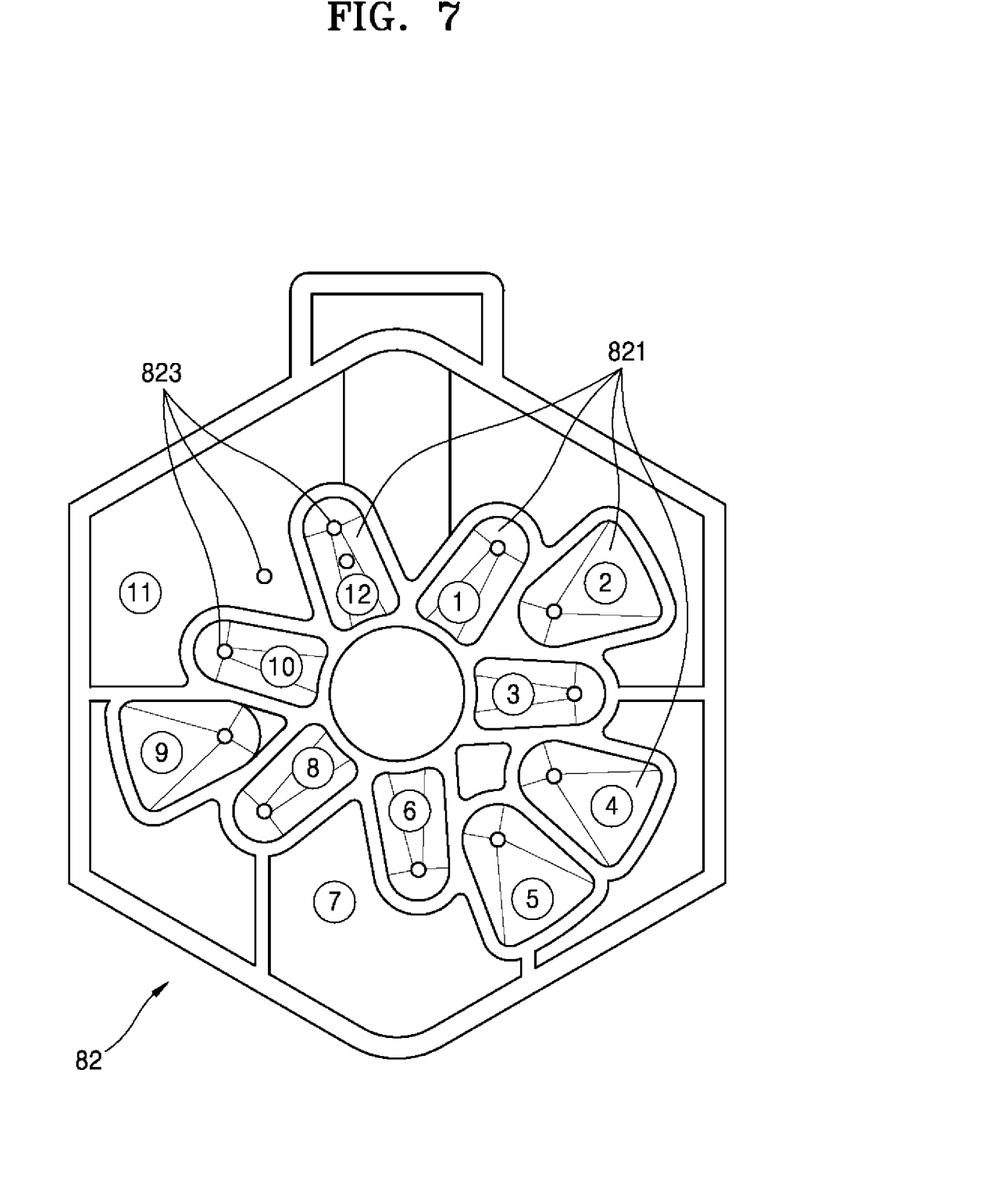
FIG. 7 is a plan view of a body forming the cartridge according to the present disclosure.
Figure 8:
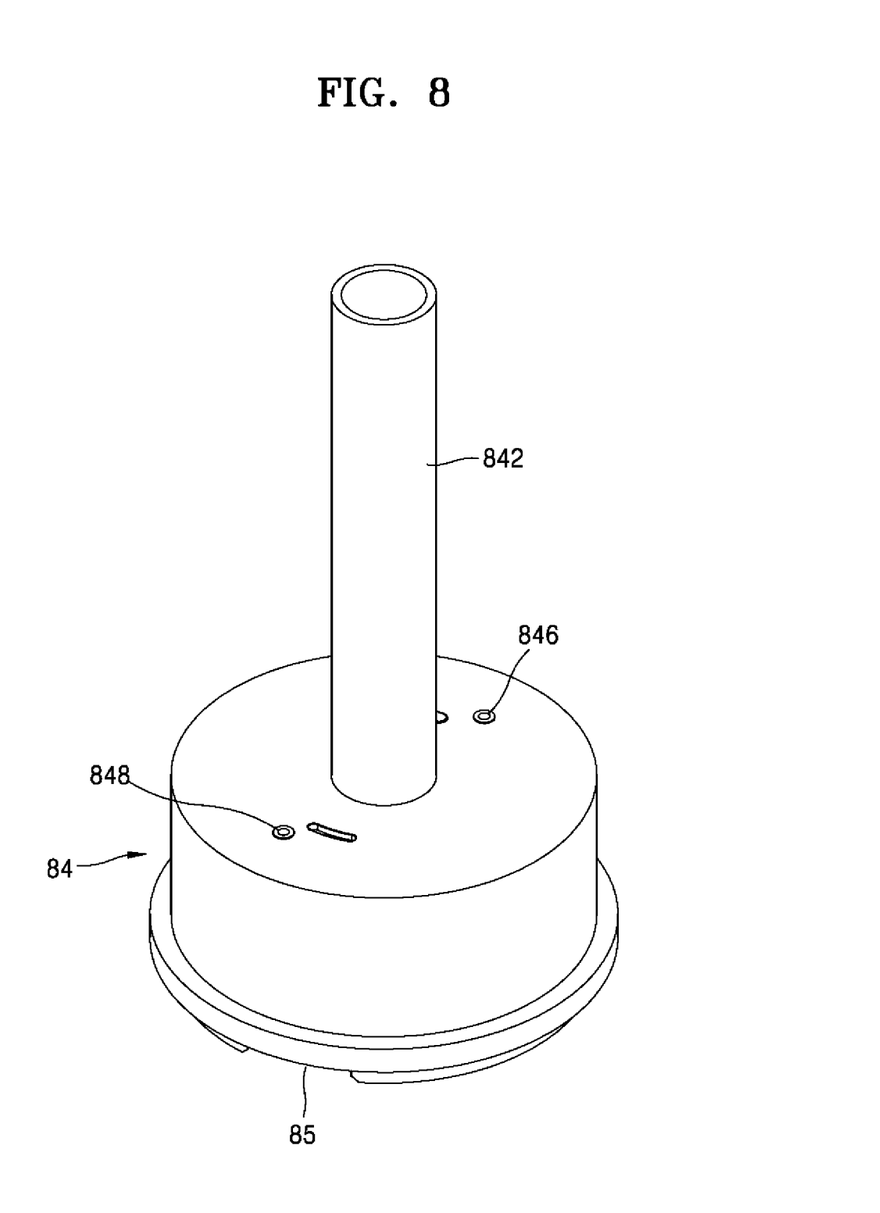
FIG. 8 illustrates a disc member according to the present disclosure.
Figure 9:
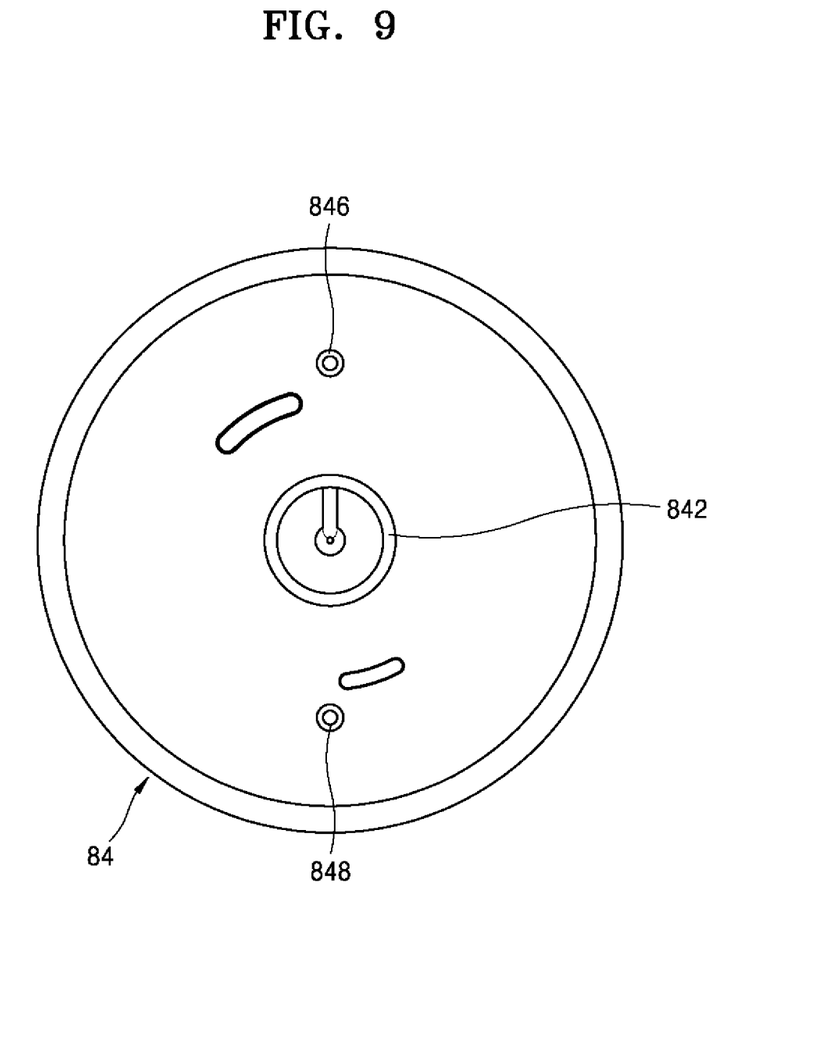
FIG. 9 is a plan view of the disc member of FIG. 8.
Figure 10:
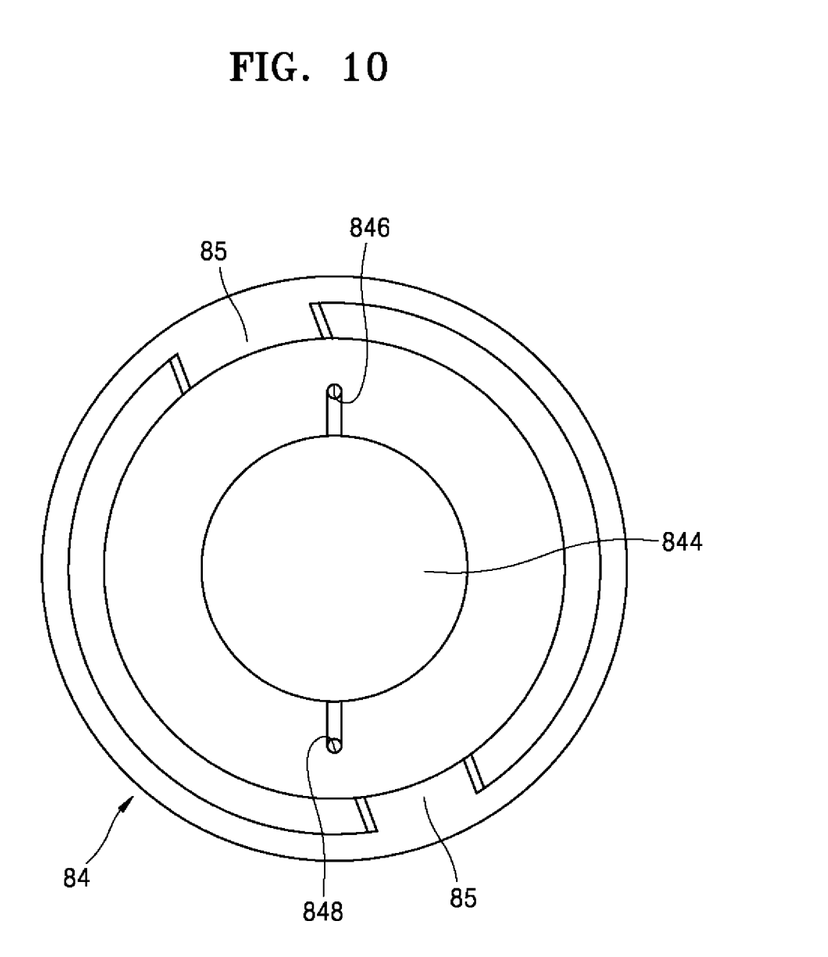
FIG. 10 is a bottom view of the disc member of FIG. 8.
Figure 11:
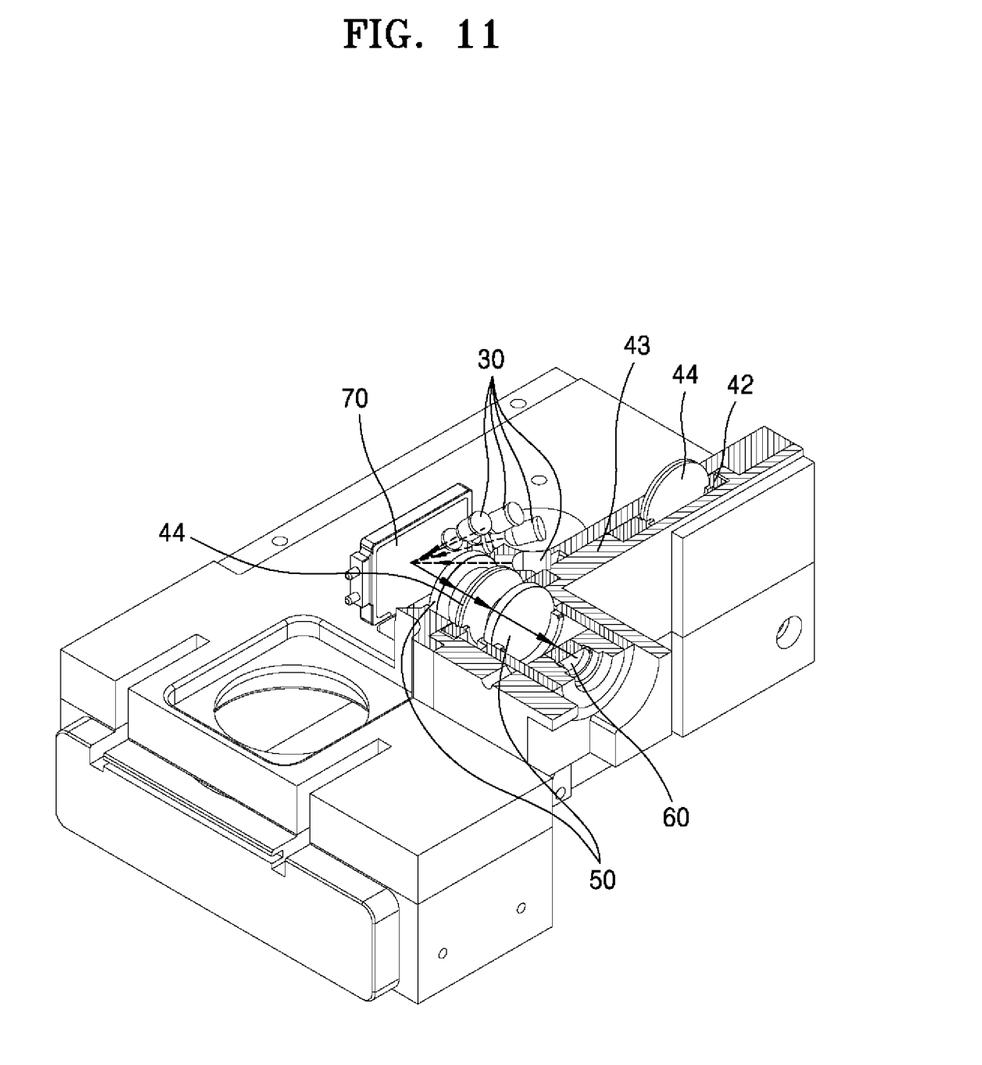
FIG. 11 illustrates the structure of a light source portion of the diagnostic apparatus of FIG. 1.
Figure 12:
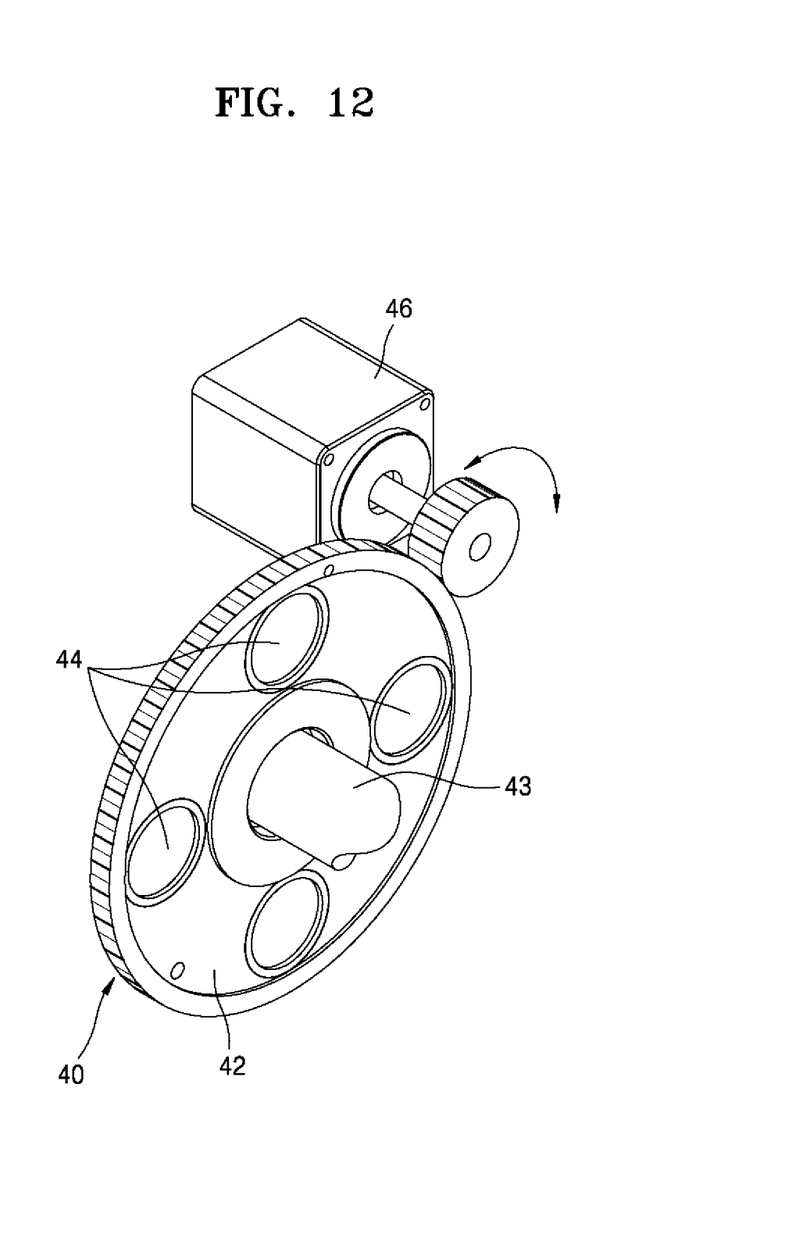
FIG. 12 illustrates a detailed structure of an optical filter portion in FIG. 11.

FIG. 1 illustrates an exterior of an in-vitro diagnostic apparatus according to an embodiment of the present disclosure. FIG. 2 illustrates a state in which a swing door of the diagnostic apparatus of FIG. 1 is opened. FIG. 3 illustrates an inner structure of the diagnostic apparatus of FIG. 1. FIG. 4 illustrates a rotating and elevating structure of a cartridge in the diagnostic apparatus of FIG. 1. FIG. 5 is a partially cut-away view illustrating an inner structure of the cartridge of FIG. 4. FIG. 6 is an exploded perspective view of constituent elements of the cartridge according to the present disclosure. FIG. 7 is a plan view of a body forming the cartridge according to the present disclosure. FIG. 8 illustrates a disc member according to the present disclosure. FIG. 9 is a plan view of the disc member of FIG. 8. FIG. 10 is a bottom view of the disc member of FIG. 8. FIG. 11 illustrates the structure of a light source portion of the diagnostic apparatus of FIG. 1. FIG. 12 illustrates a detailed structure of an optical filter portion in FIG. 11.

In the following description of the characteristics structure of a cartridge according to the present disclosure cartridge, while describing an in-vitro diagnostic apparatus having a cartridge, the characteristics of a structure of the cartridge of the in-vitro diagnostic apparatus are also described.

Referring to FIGS. 1 to 12, an in-vitro diagnostic apparatus 10 according to an embodiment of the present disclosure (hereinafter, referred to as the "in-vitro diagnostic apparatus") is an apparatus for testing the existence of a disease by extracting a biomaterial such as protein or DNA and performing a polymerase chain reaction (PCR).

The in-vitro diagnostic apparatus 10 may include a case 20, a light source portion 30, a lens portion 50, an optical filter portion 40, a photodiode sensor 60, and a cartridge 80.

The case 20 forms the exterior of the in-vitro diagnostic apparatus 10, and may be formed by combining a plurality of members. The case 20 may include an internal space, in which major constituent elements forming the in-vitro diagnostic apparatus 10 may be provided. The case 20 may be manufactured of metal or synthetic resin. A swing door 22 is provided in the case 20. The swing door 22 is provided such that it is capable of rotating within a certain angular range along one axis with respect to the case 20. The swing door 22 is used when the cartridge 80 to be described later is provided or detached. Referring to FIG. 2 or 3, a coupling structure of the swing door 22 may be more easily understood.

A pressing member 24 and a locking device 26 are provided on the swing door 22. The pressing member 24 is coupled to the swing door 22 and presses a cartridge fixing frame 90 to be described later, thereby fixing the cartridge 80 in a constant position. The pressing member 24 moves in engagement with the swing door 22. The pressing member 24 may be configured to rotate within a certain angular range with respect to the swing door 22. As such, when the pressing member 24 is configured to move with respect to the swing door 22, a type of linking structure is formed, and thus an error in a rotational path occurring during operation of the swing door 22 is offset such that the cartridge fixing frame 90 may be more firmly fixed.

The locking device 26 prevents the swing door 22 from unexpectedly opening during operation of the in-vitro diagnostic apparatus 10 since a locking pin that elastically protrudes by means of an element such as a spring is caught by the case 20.

The light source portion 30 is provided inside the case 20. The light source portion 30 is provided in a structure fixed to the case 20 and does not move. The light source portion 30 generates visible light. The light source portion 30 may employ a plurality of light-emitting diodes. In the present embodiment, four light-emitting diodes are provided. The light-emitting diodes are arranged spaced apart from one another in a circular form. The light-emitting diodes are arranged such that light emitted from the light-emitting diodes converges to a single focal point. By differentiating the wavelengths or intensities of the light emitted from each of the light-emitting diodes, the light generated by the light source portion 30 may be mutually corrected and complemented. By adopting the above structure, the light irradiated onto a biochip 70 may be controlled to exert a satisfactory fluorescence effect. The biochip 70 is filled with a biomaterial to be analyzed. PCR occurs as heat is applied to the biomaterial filled in the biochip 70. The existence of a disease may be diagnosed in real time by applying heat to the biochip 70.

The lens portion 50 focuses light that is generated by the light source portion 30 and then reflected by the biochip 70. The lens portion 50 is arranged in a path of the light reflected from the biochip 70. The lens portion 50 may include a pair of lenses. The pair of lenses are symmetrically arranged with respect to the optical filter portion 40 to be described later, and provided between the pair of lenses.

The optical filter portion 40 allows passage of only light of a specific wavelength band among the light focused by the lens portion 50. The optical filter portion 40 may include a plurality of filters 44 and a rotating disc 42 accommodating the filters 44. The filters 44 are arranged spaced apart from each other in a circular form. The filters 44 may include filters that respectively allow light having different wavelength bands to pass therethrough.

The rotating disc 42 is a wheel-shaped structure having an accommodation portion for accommodating the filters 44. In the present embodiment, as illustrated in FIG. 12, an accommodation portion capable of accommodating four filters is provided. The rotating disc 42 may be rotated by a filter rotating motor 46. A friction wheel is provided on an output shaft of the filter rotating motor 46 and coupled to the rotating disc 41 by contact with an outer circumferential surface of the rotating disc 42. In other words, the optical filter portion 40 is rotated by the filter rotating motor 46 which is fixed onto the case 20. Accordingly, when the output shaft of the filter rotating motor 46 is rotated, the friction wheel rotates the rotating disc 42, and thus a filter corresponding to a wavelength band desired by a user is selectively arranged in a path of light passing through the lens portion 50. As such, as the optical filter portion 40 is configured to rotate with respect to the biochip 70 or the lens portion 50, when different biomaterials are analyzed, it may be very easy to replace filters. In other words, the optical filter portion 40 is provided such that it is rotatable around a rotation axis 43 with respect to the biochip 70 and such that only one of the filters 44 forming the optical filter portion 40 may be selected to be located between the biochip 70 and the photodiode sensor 60 to be described later.

The photodiode sensor 60 is a sensor for detecting light passing through the optical filter portion 40. The photodiode sensor 60 generates a voltage from light. Accordingly, the existence of a disease with respect to a biomaterial may be diagnosed by the voltage output from the photodiode sensor 60.

The cartridge 80 is an apparatus for accommodating a plurality of solutions to extract a specific biomaterial to be analyzed in the biochip 70. The cartridge 80 is connected to the biochip 70. The cartridge 80 is detachably provided inside the case 20.

The cartridge 80 accommodates a biomaterial solution and a bead solution.

The cartridge 80 may include a body 82 and a disc member 84.

The body 82 may be manufactured to have a structure having a polygonal column form. The body 82 may include sample accommodating chambers 821. The sample accommodating chambers 821 may include a plurality of sample accommodating chambers. The sample accommodating chambers 821 are formed in a space which is sectioned to accommodate a plurality of fluids in a distributed manner. A fluid input/output port 823 is provided in a bottom portion of each of the sample accommodating chambers 821. The fluid input/output port 823 is formed as a hole penetrating through the bottom portion of each of the sample accommodating chambers 821. A center portion of the body 82 forms a vertically penetrating tube structure. A cylinder portion 842 of the disc member 84 to be described later is rotatably coupled to the center portion of the body 82. A cover covering the sample accommodating chambers 821 is provided in an upper portion the body 82.

The disc member 84 is rotatably coupled to the body 82. The disc member 84 may be rotated with respect to the body 82 by a disc rotating motor 86. The disc member 84 is rotated by being caught by a rotation member 88. The rotation member 88 is provided with a protruding step 89, and a clutch groove portion 85 that is caught by the protruding step 89 is provided on a lower surface of the disc member 84. As the protruding step 89 and the clutch groove portion 85 are coupled to each other, the disc member 84 and the rotation member 88 are rotated as one body. The rotation member 88 is connected to the disc rotating motor 86 by means of a device such as a belt.

The disc member 84 may include the cylinder portion 842 and a sample mixing chamber 844.

The cylinder portion 842 has a hollow tube form, is coupled to the body 82, and vertically penetrates through the center portion of the body 82. A syringe piston 850 is slidably provided in the cylinder portion 842.

The sample mixing chamber 844 is provided under the cylinder portion 842. The sample mixing chamber 844 may be selectively connected to the fluid input/output port 823 via a fluid path 846 or an injection path 848, which are described later. As the disc member 84 rotates, the fluid path 846 or the injection path 848 may be selectively connected to the fluid input/output port 823 provided in any one of the sample accommodating chambers 821.

The fluid path 846 is a path that is selectively connected to the sample mixing chamber 844. In other words, according to the rotation of the disc member 84, any one of the sample accommodating chambers 821 and the sample mixing chamber 844 are connected to each other by the fluid path 846. In other words, the fluid path 846 is selectively connected to the fluid input/output port 823. The fluid path 846 is connected to the cylinder portion 842.

The injection path 848 is a path through which a biomaterial prepared in the sample mixing chamber 844 is injected into the biochip 70. The injection path 848 selectively connects the sample mixing chamber 844 with the biochip 70 according to the rotation of the disc member 84.

The syringe piston 850 is coupled to the cylinder portion 842 such that the syringe piston 850 is capable of being slidably elevated along an inner circumferential surface of the cylinder portion 842. The syringe piston 850 is connected to a rod 852. The rod 852 is provided such that it is capable of being elevated by an elevation motor 854. The rod 852 and the elevation motor 854 may be connected to each other such that the syringe piston 850 elevates along the cylinder portion 842 by means of a ball screw device 857 that converts a rotation motion to a linear motion. In other words, the syringe piston 850 is moved up and down by the elevation motor 854.

Transfer of fluid between the sample accommodating chambers 821 and the sample mixing chamber 844 or between the sample mixing chamber 844 and the biochip 70 is possible due to pressure generated by an elevation operation of the syringe piston 850.

An electromagnet 100 is provided in a lower portion of the cartridge 80. The electromagnet 100 generates a magnetic force only when power is supplied. The electromagnet 100 applies a magnetic force to a bead solution that increases purity of the biomaterial extracted from the cartridge 80. Since the electromagnet 100 generates a magnetic force only when a user needs the magnetic force, the operation of the bead solution may be selectively controlled.

The electromagnet 100 is provided with a heating wire (not shown) for heating the lower portion of the cartridge 80. The heating wire may be provided as a heating pattern printed on a surface of the electromagnet 100 to generate electrical resistance heat. The heating wire is not limited to the heating pattern and other well-known configurations thereof may be employed. The heating wire heats the solution that is input to the sample mixing chamber 844 provided in the lower portion of the cartridge 80 to an appropriate temperature, to promote a reaction.

The cartridge 80 is detachably provided inside the case 20 by being accommodated in the cartridge fixing frame 90.

The cartridge fixing frame 90 is a member for fixing the body 82 not to move, while supporting a lower portion of the body 82. The cartridge fixing frame 90 is fixed to the case 20 by the pressing member 24 provided in the swing door 22 of the case 20. The cartridge fixing frame 90 is a member that directly receives pressure applied by the pressing member 24, and protects the cartridge 80 by preventing the cartridge 80 from being directly coupled to the pressing member 24.

In the following description, the operation and effects of the in-vitro diagnostic apparatus 10 including the above-described elements are described in detail along with a transfer process of a biomaterial.

According to the present disclosure, when a diagnosis is made based on a biomaterial by using the in-vitro diagnostic apparatus 10, a process of extracting a biomaterial for diagnosis from the cartridge 80 is first performed. In other words, the sample accommodating chambers 821 provided in the cartridge 80 accommodate a plurality of solutions as shown in the following table. The solutions listed in the table are merely examples and may vary according to the type of a biomaterial to be used for diagnosis. In Table1, serial numbers correspond to the numbers of the sample accommodating chambers 821 indicated by circled numbers in FIG. 7, for convenience of explanation.

TABLE 1

| Serial No. | Name (Abbr) | Solution Name | Purpose |
|---|---|---|---|
| ① | LB1 | LYSIS BUFFER 1 | Accommodation place for LYSIS BUFFER 1 |
| ② | LB2 | LYSIS BUFFER 2 | Accommodation place for LYSIS BUFFER 2 |
| ③ | ET | ETHANOL | Accommodation place for ETHANOL |
| ④ | BD | BEAD SOLUTION | Accommodation place for BEAD SOLUTION |
| ⑤ | WB1 | WASHING BUFFER 1 | Accommodation place for WASHING BUFFER 1 |
| ⑥ | WB2 | WASHING BUFFER 2 | Accommodation place for WASHING BUFFER 2 |
| ⑦ | EB | ELUTION BUFFER | Accommodation place for ELUTION BUFFER |
| ⑧ | MC1 | MIXING CHAMBER 1 | MIXING place used for LYSIS |
| ⑨ | MC2 | MIXING CHAMBER 2 | Place used for WASHING |
| ⑩ | WAC | WASTE CHAMBER | Place for disposed solution |
| ⑪ | WS | WORKING SPACE | Fluid transfer space. Place where BEAD and ELUTION are performed |
| ⑫ | SC | SAMPLE CHAMBER | First accommodation place for SAMPLE |

When a specific solution is to be used from one of the sample accommodating chambers 821, the disc rotating motor 86 is rotated. Accordingly, the rotation member 88 is rotated. Since the protruding step 89 provided in the rotation member 88 and the clutch groove portion 85 provided in the disc member 84 are coupled to each other, the disc member 84 is rotated. As the disc member 84 is rotated by a certain angle, the fluid path 846 is connected to the fluid input/output port 823 provided in a specific chamber among the sample accommodating chambers 821. Then, the elevation motor 854 is operated such that the syringe piston 850 is moved upward. As the syringe piston 850 ascends, negative pressure is generated. Accordingly, the solution the specific chamber among the sample accommodating chambers 821 is transferred to the cylinder portion 842 along the fluid path 846. Then, the operation of the syringe piston 850 is stopped, and the disc rotating motor 86 is operated to rotate the disc member 84. The fluid path 846 of the disc member 84 is connected to, for example, the fluid input/output port 823 provided in ⑪ WORKING SPACE. Then, the syringe piston 850 is lowered. As the syringe piston 850 descends, the solution in the cylinder portion 842 is transferred to ⑪ WORKING SPACE via the sample mixing chamber 844. Next, the disc member 84 is rotated again such that one of the sample accommodating chambers 821 accommodating ⑦ ELUTION BUFFER is aligned with the fluid path 846. By repeating the above processes, ⑦ ELUTION BUFFER may be transferred to the ⑪ WORKING SPACE. Accordingly, a necessary bio solution may be extracted by repeating the above processes. Then, a mixed solution of the solution to be extracted and a bead solution is input to the sample mixing chamber 844. The electromagnet 100 is operated to fix a bio solution containing a specific component. In this state, the syringe piston 850 is lowered and then an unnecessary solution component is disposed into ⑩ WASTE CHAMBER. The injection path 848 is connected to the biochip 70. The current of the electromagnet 100 is cut off so that the operation of the bead solution is removed. In this state, the syringe piston 850 is lowered, and thus the bio solution accommodated in the sample mixing chamber 844 is injected into the biochip 70.

As such, since the cartridge for an in-vitro diagnostic apparatus according to the present disclosure includes functions of extracting a biomaterial to be diagnosed and injecting the extracted biomaterial into the biochip within the diagnostic apparatus, continuity of biochip preparation and diagnosis processes may be maintained, and efficiency of diagnosis may be improved much.

During the PCR that occurs while applying heat to the biochip 70 prepared through the above processes, the biochip 70 is in real time or periodically irradiated with visible light. In this state, the amount of light reflected from the biochip 70 is measured.

A process of analyzing the biochip 70 is described below.

The light source portion 30 generates visible light of a specific wavelength band and emits the visible light to the biochip 70. Light reflected from the biochip 70 is focused by the lens portion 50, and filtered by the optical filter portion 40 to arrive at the photodiode sensor 60. Accordingly, a voltage is generated and analysis is performed. In this process, as the optical filter portion 40 is rotatably provided with respect to the biochip 70, one of the filters 44 corresponding to the type of a biomaterial to be analyzed may be easily selected.

As such, since the cartridge for an in-vitro diagnostic apparatus according to the present disclosure includes a body having a sample accommodating chamber sectioned into a plurality of spaces, and a disc member rotatably coupled to the body and selectively transferring a fluid including a biomaterial between the sample accommodating chamber and a sample mixing chamber, by using a syringe, the biomaterial prepared in the sample mixing chamber may be directly injected into the biochip. Accordingly, without separately preparing a biochip, continuous performance from preparation to diagnosis of the biochip within a single diagnostic apparatus may be possible.

In the in-vitro diagnostic apparatus according to an embodiment of the present disclosure, by applying an electromagnet to a magnetic system magnetically interacting with a bead for accurate extraction of a biomaterial to be diagnosed, a magnetic force is generated only when necessary, and thus accuracy of extraction of a bio sample may be improved.

Furthermore, in the in-vitro diagnostic apparatus according to an embodiment of the present disclosure, even when the type of a biomaterial to be diagnosed is changed, an optical filter for well passing a wavelength of light generated from the biomaterial may be rapidly and easily replaced by a rotatable optical filter portion.

The above-described embodiments are provided to further completely explain the present disclosure to one of ordinary skill in the art to which the present disclosure pertains. However, the present disclosure is not limited thereto and it will be understood that various changes in form and details may be made therein without departing from the spirit and scope of the following claims.

MODE OF THE INVENTIVE CONCEPT

According to an aspect of the present disclosure, an in-vitro diagnostic apparatus includes a cartridge including a body and a disc member, wherein a biochip is detachably coupled to the body, the body includes a plurality of sample accommodating chambers including a sectioned space for accommodating a plurality of fluids in a distributed manner, and the disc member is rotatably coupled to the body, wherein the disc member includes a cylinder portion and a sample mixing chamber, wherein the cylinder portion has a hollow tube form, is coupled to the body, and vertically penetrates through a center portion of the body, and the sample mixing chamber is located under the cylinder portion, wherein a fluid input/output port is provided in a bottom portion of each of the plurality of sample accommodating chambers, wherein the sample mixing chamber includes a fluid path and an injection path, the fluid path selectively connectable to the fluid input/output port, and the injection path connecting the sample mixing chamber with the biochip to allow a biomaterial prepared in the sample mixing chamber to be injected into the biochip, wherein a syringe piston is coupled to the cylinder portion and is configured to slidably elevate along an inner circumferential surface of the cylinder portion, wherein the disc member is rotatable by a disc rotating motor with respect to the body, wherein the disc member is rotatable by being caught by a rotation member, wherein the rotation member includes a protruding step, and a clutch groove portion is provided on a lower surface of the disc member, the clutch groove portion being caught by the protruding step; a case; a light source portion provided inside the case and generating visible light; a lens portion focusing light emitted from the light source portion and reflected by the biochip; an optical filter portion allowing only light of a specific wavelength band among light focused by the lens portion to pass therethrough; a photodiode sensor configured to detect light that passed through the optical filter portion; a disc rotating motor configured to rotate the disc member with respect to the body; and an elevation motor configured to elevate the syringe piston, wherein the optical filter portion is rotatable by a filter rotating motor that is fixed to the case, wherein the light source portion includes a plurality of light-emitting diodes arranged spaced apart from each other in a circular form, the plurality of light-emitting diodes being arranged such that light emitted from the plurality of light-emitting diodes converges to a single focal point.

The cartridge may be detachably provided inside the case, the in-vitro diagnostic apparatus including an electromagnet in a lower portion of the cartridge, the electromagnet being configured to apply a magnetic force to a bead solution that increases purity of a biomaterial extracted from the cartridge.

A plurality of filters allowing different wavelength bands of light to pass therethrough may be arranged spaced apart from one another in a circular form in the optical filter portion, and the optical filter portion may be configured to rotate around a rotation axis with respect to the biochip to allow only one of the plurality of filters forming the optical filter portion to be selected to be between the biochip and the photodiode sensor.

The lens portion may include a pair of lenses symmetrically arranged with respect to the optical filter portion provided between the pair of lenses.

The invention claimed is:

1. An in-vitro diagnostic apparatus comprising:
a case having an interior space, the interior space comprising:
a cartridge comprising a body and a disc member, wherein a biochip is connected to the body, wherein the body includes a plurality of sample accommodating chambers for accommodating a plurality of fluids in a distributed manner, and wherein the disc member is rotatably coupled to the body,
the disc member comprising a cylinder portion and a sample mixing chamber, wherein the cylinder portion has a hollow tube form, is coupled to the body, and vertically penetrates through a center portion of the body, and wherein the sample mixing chamber is located under the cylinder portion,
a fluid input/output port, wherein the fluid input/output port is provided in a bottom portion of each of the plurality of sample accommodating chambers,
the sample mixing chamber comprising a fluid path and an injection path, wherein the fluid path is selectively connectable to the fluid input/output port, and wherein the injection path selectively connects the sample mixing chamber with the biochip, thereby allowing a biomaterial prepared in the sample mixing chamber to be injected into the biochip,
a syringe piston, wherein the syringe piston is coupled to the cylinder portion and is configured to slidably elevate along an inner circumferential surface of the cylinder portion,
wherein the disc member is rotatable with respect to the body by a disc rotating motor, wherein the disc rotating motor is connected to a rotation member by a belt,
wherein the rotation member includes a protruding step, and a clutch groove portion is provided on a lower surface of the disc member, and when the clutch groove portion and the protruding step are coupled to one another, the disc member and the rotation member are rotated;
a light source portion, wherein the light source portion generates visible light toward the biochip;
a lens portion comprising a pair of lens that are symmetrically arranged with respect to an optical filter portion, wherein the lens portion focuses light emitted from the light source portion and reflected by the biochip;
an optical filter portion comprising a plurality of filters and a rotating disc accommodating the plurality of filters, wherein the optical filter portion allows only light of a specific wavelength band among light focused by the lens portion to pass there through;
a photodiode sensor configured to detect light that passes through the optical filter portion;
and an elevation motor configured to elevate the syringe piston, wherein the optical filter portion is rotatable by a filter rotating motor that is fixed to the case, wherein the light source portion comprises a plurality of light-emitting diodes arranged spaced apart from each other in a circular form, the plurality of light-emitting diodes being arranged such that light emitted from the plurality of light-emitting diodes converges to a single focal point.

2. The in-vitro diagnostic apparatus of claim 1, further comprising an electromagnet in the cartridge, the electromagnet being configured to apply a magnetic force to a bead solution that increases purity of a biomaterial extracted from the cartridge.

3. The in-vitro diagnostic apparatus of claim 1, wherein a plurality of filters allowing different wavelength bands of light to pass therethrough are arranged spaced apart from one another in a circular form in the optical filter portion, and the optical filter portion is configured to rotate around a rotation axis with respect to the biochip to allow only one of the plurality of filters forming the optical filter portion to be selected to be between the biochip and the photodiode sensor.

4. The in-vitro diagnostic apparatus of claim 1, wherein the cartridge is detachably provided inside the case by being accommodated in a cartridge fixing frame.

5. The in-vitro diagnostic apparatus of claim 1, wherein the cartridge fixing frame is fixed to the case by a pressing member that is provided on a swing door provided in the case.

* * * * *